United States Patent [19]

Pallone et al.

[11] 4,296,764
[45] Oct. 27, 1981

[54] HAIR WAVING AND STRAIGHTENING METHOD

[75] Inventors: Thomas J. Pallone, Monroe; Mark Lynch, Southbury; Janice E. Corvino, Stratford; John P. McCook, Madison, all of Conn.

[73] Assignee: Chesebrough-Pond's Inc., Greenwich, Conn.

[21] Appl. No.: 107,746

[22] Filed: Dec. 26, 1979

[51] Int. Cl.$^3$ ............................................. A45D 7/00
[52] U.S. Cl. ..................................................... 132/7
[58] Field of Search ............... 132/7; 424/71; 8/127.6

[56] References Cited

U.S. PATENT DOCUMENTS 2,836,185  5/1958  Hervey .................................... 132/7
3,173,842  3/1965  Hervey .................................... 132/7
3,533,417  10/1970 Bartoszewicz .......................... 132/7
3,865,930  2/1975  Abegg ..................................... 132/7

Primary Examiner—G. E. McNeill
Attorney, Agent, or Firm—Morgan, Finnegan, Pine, Foley & Lee

[57] ABSTRACT

A process for the waving or straightening of hair by treating with an alkaline bisulphite and or sulfite preparation followed by neutralizing with hydrogen peroxide is improved by using an aqueous neutralizing solution in which the hydrogen peroxide is present in a concentration of from 0.65 to 3.4% by weight and proportional to the concentration by weight of available sulfur dioxide in the waving/straightening solution used prior to neutralization. The process avoids certain disadvantages associated with the prior art.

11 Claims, No Drawings

HAIR WAVING AND STRAIGHTENING METHOD

BACKGROUND OF THE INVENTION

Chemical preparations for use in the permanent or cold waving and straightening of hair are known. Among these are alkaline compositions containing a bisulphite or sulfite compound. Such compositions are disclosed in U.S. Pat. No. 2,836,185, U.S. Pat. No. 3,864,476 and British Pat. No. 849,045. Bisulphite/sulfite hair treating preparations are to be distinguished from waving and/or straightening preparations based on the use of other compounds such as ammonium thio compounds, thioglycolic acid and thiols.

When waving or straightening hair with alkaline bisulphite or sulfite preparations particularly, sulphur and hydrogen bonds as well as various salt linkages within the hair are broken upon contacting with the waving and straightening preparation. To reestablish the broken bonds in the newly waved or straightened position and thus "lock in" and set the hair, oxidizing preparations such as those containing hydrogen peroxide are often used.

Special mention is made of the compositions disclosed in U.S. Pat. No. 3,864,476, incorporated herein by reference. This describes alkaline solutions for the waving and straightening of hair, comprising acidic metal bisulphite, alkali metal borate, alkali metal carbonate, alkanolamine and water. These are disclosed for use in combination with a neutralizing solution which contains hydrogen peroxide.

The foregoing preparations do not always provide the desired degree of curl tightness and springiness and the hair does not retain its curl for as long a period as desirable. Also, the use of hydrogen peroxide in conjunction with the alkaline bisulphite preparation sometimes results in hair lightening, which is undesirable.

OBJECTS OF THE INVENTION

It is an object of this invention to provide an improved process for the cold waving or straightening of hair.

It is another object of this invention to provide a process for the cold waving or straightening of hair which provides a tighter, springier and longer-lasting curl with a hair waving use, and longer-lasting straight hair with a hair straightening use.

It is another object of this invention to provide a process for the cold waving or straightening of hair which uses a hydrogen peroxide neutralizer having less tendency to produce hair lightening.

These objects as well as other objects which will be apparent from the following description and from the examples, are achieved by the invention now described.

SUMMARY OF THE INVENTION

Briefly described, this invention comprises an improvement in a process for the cold waving or straightening of hair comprising treating the hair with an alkaline solution containing a bisulphite and/or sulfite compound followed by treating with a hydrogen peroxide solution. The improvement comprises using an aqueous solution of hydrogen peroxide the concentration of which, typically 0.65% to 3.4% by weight, is in proportion to the weight percentage of available sulfur dioxide of the waving/straightening solution in a ratio between 0.34(1:2.9) and 0.26 (1:3.8) of $H_2O_2$ to sulfur dioxide (present as a sulfite or bisulfite salt).

It has now been surprisingly found that the use of hydrogen peroxide in the foregoing specified concentrations and ratios in a process as described, provides tighter, springier longer-lasting results which is unexpected, and reduced hair lightening or bleaching. Significantly, these same results are not obtained when the concentrations and ratios are appreciably above or below the 0.65 to 3.4% by weight range for the hydrogen peroxide solution and the 0.26 (1:3.8) to 0.34 (1:2.9) ratio of percent by weight of hydrogen peroxide in the neutralizer to the percent by weight of available sulfur dioxide of the waving/straightening solution, as is demonstrated in the examples.

DETAILED DESCRIPTION OF THE INVENTION

A hair curling and straightening composition for use in this invention comprises an aqueous alkaline bisulfite solution containing acidic metal bisulphite, alkali metal borate, alkali metal carbonate, alkanolamine and water.

The acid metal bisulphites may be selected from any materials commonly employed for this purpose, and preferably are chosen from among alkali metal bisulphites such as sodium bisulphite ($NaHSO_3$), potassium metabisulphite ($K_2S_2O_5$) and potassium bisulphite ($KHSO_3$). These may be used together with or substituted by a sulphite compound, such as sodium sulphite ($Na_2SO_3$) or potassium sulphite ($K_2SO_3$), as alternate sources of sulphur dioxide to help produce the desired waving or straightening effect.

The alkali metal borate constituent is usually sodium borate or potassium borate.

The metal carbonate constituent is usually sodium carbonate, sodium bicarbonate or potassium carbonate, or mixtures of any of these.

Examples of the alkanolamines which may be used in the hair waving and straightening composition include, without limitation, monoethanolamine, diethanolamine, triethanolamine, triethylenetetramine and triisopropanolamine, or combinations thereof.

The same formulation is suitable for both hair waving and hair straightening.

In general, the ingredients of the hair waving and straightening solution vary widely within certain preferred ranges which may be expressed as follows:

| Ingredients | Amount, % by weight |
| --- | --- |
| Acidic metal bisulphite (expressed as available $SO_2$) | 1.9 to 13.0 |
| Alkali metal borate | 0.6 to 8.2 |
| Alkali metal carbonate | 0.6 to 8.2 |
| Alkanolamine | 1.7 to 9.8 |
| Water | q.s. to 100% |

More usually, the hair waving and straightening solution is compounded within narrower limits as follows:

| Ingredients | Amount, % by weight |
| --- | --- |
| Sodium bisulphite (expressed as available $SO_2$) | 3.5 to 5.0 |
| Sodium borate | 2.0 to 4.0 |
| Sodium carbonate | 1.3 to 3.5 |
| Monoethanolamine | 5.3 to 6.5 |
| Diethanolamine | 1.4 to 1.8 |

| Ingredients | Amount, % by weight |
| --- | --- |
| Water | q.s. to 100% |

The inclusion of a wetting agent or agents may be added to lower the surface tension of the solution and enhance the absorption of the active ingredients into the hair shafts. Such materials are known to those skilled in the art and include, illustratively, sorbitan monolaurate, polyoxyethylene lauryl ethers, gelatin, polyoxyethylene monostearate, polyethylene glycol monostearate, triethanolamine oleate, polyoxyethylene alkyl phenol, polyoxyethylene alkyl aryl ether, acyl amido glycine betaine, diethanolamine-$C_{21}$ dicarboxylate, diethanolamine cocamide, and diethanolamine dodecylbenzenesulfonate. An example of a suitable commercially available material is Triton X-102, Rohm & Haas Company, alkylaryl polyether alcohol.

The wetting agent can be used without limitation, and is preferably employed in amounts of from about 0.1 to 3.5 percent by weight, based on the total weight of the solution.

The foregoing compositions are characterized by a pH within the range between 8 and 12.5, and a sulphur dioxide content within the range between 1.9 and 13.0 percent by weight.

Other ingredients, selected from among known materials, may also be included in the hair waving and straightening solution for their conventionally employed purposes. These include fragrances, coloring agents, thixotropic agents, skin or hair conditioners, slip imparting agents, opacifiers, stabilizers, etc.

Preferably, the compositions are compounded by dissolving the alkanolamine in the correct amount of water and then sequentially dissolving the alkali metal borate, the alkali metal carbonate, and the acidic metal bisulphite. Any optional additional ingredients may thereafter be added to the solution.

The neutralizer for use in this invention is prepared by dissolving a suitable amount of hydrogen peroxide in water, preferably deionized water, to form a solution having a hydrogen peroxide concentration of from 0.65 to 3.4% by weight and with a ratio of between 0.34 (1:2.9) and 0.26 (1:3.8) to the available sulfur dioxide from the wave lotion employed. The pH of the solution is within the range 2.0 to 5.0, preferably. Adjustment to the desired pH may be made by adding a suitable amount of phosphoric acid, citric acid, or other acids which will not cause hydrogen peroxide to become unstable.

In practice, this invention may be carried out by use of the procedures described below, which are preferred for use in this invention.

When hair straightening is desired, the following procedure is employed:

The hair is first thoroughly washed with a shampoo or soap. Any conventional shampoo or soap may be used. Afterwards, the hair is dried, as by towelling.

An alkaline bisulphite and/or sulfite containing solution, such as described above, is then combed through the hair for a period of from thirty to one-hundred twenty minutes, and the hair is thereafter rinsed with ordinary tap water.

Immediately after rinsing, the neutralizer is applied to the hair. In accordance with this invention, this neutralizer comprises an aqueous solution of hydrogen peroxide in a concentration within the range 0.65 to 3.4% by weight. The hydrogen peroxide solution is permitted to remain in contact with the hair for a period of from five to ten minutes. During this period, it is preferred to comb the hair occasionally to ensure adequate distribution of the neutralizer. The hydrogen peroxide solution is then rinsed away with water and the hair is dried without setting, by use of a hair dryer, for example.

When hair waving or curling is desired, the following procedure is employed:

The hair is first washed with shampoo or soap and dried as described above. The alkaline bisulphite and/or sulfite containing hair treating solution is then combed through the hair. After wetting in this manner, the hair is rolled about permanent wave rods, curlers or pegboards of any conventional design. The hair is then wetted with additional alkaline bisulphite and or sulfite solution. A plastic cap is applied and the hair thus curled and covered is maintained for a period of from thirty to one-hundred twenty minutes, depending upon the particular characteristics of the hair and the degree of curl or wave desired. This period may be shortened by applying heat to the hair as by a hair dryer, to hasten processing. After this period, the hair is rinsed with water while still in the rods or curlers. The hair is then blotted dry with a towel and the hydrogen peroxide solution is applied. The peroxide is left on for a period of five to ten minutes, to permit setting to take place. Thereafter, the curlers are removed and the hair is rinsed, dried and styled as desired.

DESCRIPTION OF THE PREFERRED EMBODIMENTS

The invention is further illustrated in the following examples, which are not intended to be limiting.

EXAMPLE 1

A hair waving solution having the following composition is prepared:

| Ingredients | Amount, % by weight |
| --- | --- |
| Sodium bisulphite | 6.46 |
| Sodium borate | 2.15 |
| Sodium carbonate | 1.44 |
| Monoethanolamine | 5.90 |
| Diethanolamine | 1.57 |
| Water | q.s. to 100% |

The solution has a pH of 10.00, and contains 4.3% by weight of available sulfur dioxide.

The solution is combed through hair which has been previously washed. After the hair has been thoroughly wetted in this manner, it is rolled about curlers and wetted with small additional amounts of the solution. The hair is permitted to remain rolled up in the curlers for a period of about forty-five to sixty minutes, then rinsed with water while the curlers are still on and blotted dry with a towel. After towelling, the following neutralizing solution is applied:

| Hydrogen peroxide | 1.3% by weight |
| --- | --- |
| Phosphoric acid | to pH 3.50 |
| Deionized water | q.s. to 100% |

(Ratio of hydrogen peroxide to available sulfur dioxide = 0.30, or stated another way, 1:3.3)

The hydrogen peroxide solution is permitted to remain in contact with the hair for a period of from about five to ten minutes. The curlers are then removed and the hair is rinsed with water, dried and styled.

It is observed that the curls have excellent tightness and springiness. The hair has not undergone any noticeable change in color. The tightness results are observed to be long lasting.

For purposes of comparison, the same hair waving and straightening solution is applied in the manner described, followed by treating with a hydrogen peroxide solution having a peroxide concentration of 1.0% by weight in one case and 1.6% by weight in another case. This gives a ratio of hydrogen peroxide to available sulfur dioxide of 0.23, in the first case, and 0.37, in the second case, which are outside the ratios of this invention. It is observed that the curl tightness is inferior, in each case, to that obtained by use of the process of the invention. Moreover, some hair color lightening has taken place in the comparison test.

EXAMPLE 2

The procedure of Example 1 is repeated, except that the following neutralizer solution is used. This gives a hydrogen peroxide to available sulfur dioxide ratio of 0.26 (1:3.8) for the neutralizing step:

| Hydrogen peroxide | 1.1% by weight |
|---|---|
| Phosphoric acid | to pH 3.50 |
| Deionized water | q.s. to 100% |

Substantially the same results as in Example 1 are obtained.

EXAMPLE 3

The procedure of Example 1 is repeated, using, in sequence, the following hair waving/straightening composition and the following neutralizing composition:

| Hair Waving/Straightening | |
|---|---|
| | Percent by Weight |
| Sodium bisulphite | 9.69 |
| Sodium borate | 3.22 |
| Sodium carbonate | 2.16 |
| Monoethanolamine | 5.90 |
| Diethanolamine | 1.57 |
| Water | q.s. to 100% |
| pH | 9.5 to 10.5 |
| Available sulfur dioxide | 6.5% by weight |

| Neutralizer | |
|---|---|
| Hydrogen peroxide | 2.0% by weight |
| Phosphoric acid | to pH 3.50 |
| Water (deionized) | q.s. to 100% |

Ratio of hydrogen peroxide to available sulfur dioxide = 0.31 (1:3.3)

Substantially the same results as in Example 1 are obtained.

EXAMPLE 4

Example 3 is repeated, using as the neutralizer the following composition:

| Hydrogen peroxide | 1.7% by weight |
|---|---|
| Phosphoric acid | tp pH 3.50 |
| Water (deionized) | q.s. to 100% |

Ratio of available hydrogen peroxide to available sulfur dioxide = 0.26 (1:3.8)

Substantially the same results as in Example 3 are obtained.

Other modifications and variations of the invention are possible in the light of the description provided. It is to be understood, therefore, that changes may be made in the specific embodiments without departing from the scope and principles of the invention as defined in the appended claims and without sacrificing the chief benefits.

We claim:

1. In a process for the cold waving or straightening of hair, the improvement which serves to provide longer-lasting results with less tendency to undergo hair lightening and increased tightness and springiness when used as a waving solution, comprising contacting the hair with an alkaline cold waving or straightening solution containing acidic metal sulfite and/or acidic metal bisulfite, capable of generating sulfur dioxide, followed by treating with an aqueous neutralizer solution having a pH between 2.0 and 5.0 and containing hydrogen peroxide in a concentration between 0.65 and 3.4 percent by weight giving a ratio of weight percent hydrogen peroxide in the neutralizer to weight percent sulfur dioxide from the waving/straightening solution of between 0.26 and 0.34.

2. The process of claim 1, in which the cold waving or straightening solution contains acidic metal bisulphite, and/or sulfite, alkali metal borate, an alkali metal carbonate, alkanolamine and water.

3. The process of claim 2, in which the hair waving and straightening solution has the following composition:

| available sulfur dioxide (in the form of acidic metal bisulphite) | 1.9 to 13.0% by weight |
|---|---|
| alkali metal borate | 0.6 to 8.2% by weight |
| alkali metal carbonate | 0.6 to 8.2% by weight |
| alkanolamine | 1.7 to 9.8% by weight |
| water | q.s. to 100% |

4. The process of claim 2, in which the hair waving and straightening solution has the following composition:

| sodium bisulphite | 9.69% by weight |
|---|---|
| sodium borate | 3.22% by weight |
| sodium carbonate | 2.16% by weight |
| monoethanolamine | 5.90% by weight |
| diethanolamine | 1.57% by weight |
| water | q.s. to 100% by weight |

5. The process of claims 2 or 4, in which the hair waving and straightening solution also contains a wetting agent.

6. The process of claims 2 or 4, in which the hydrogen peroxide solution has a peroxide concentration of 1.9 percent by weight and a pH of 3.50 when used as a neutralizer for a waving/straightening solution with 6.5% by weight of available sulfur dioxide.

7. The process of claims 2 or 4, in which the hydrogen peroxide solution has a peroxide concentration of 1.7 percent by weight and a pH of 3.50 when used as a neutralizer for a waving/straightening solution with 6.5% by weight of available sulfur dioxide.

8. The process of claim 2, in which the hair waving and straightening solution has the following composition:

| | |
|---|---|
| sodium bisulphite | 6.46% by weight |
| sodium borate | 2.15% by weight |
| sodium carbonate | 1.44% by weight |
| monoethanolamine | 5.90% by weight |
| diethanolamine | 1.57% by weight |
| water | q.s. to 100% by weight |

9. The process of claims 2 or 8, in which the hair waving and straightening solution also contains a wetting agent.

10. The process of claims 2 or 8, in which the hydrogen peroxide solution has a peroxide concentration of 1.3 percent by weight and a pH of 3.50 when used as a neutralizer for a waving/straightening solution with 4.3% by weight of available sulfur dioxide.

11. The process of claims 2 or 8, in which the hydrogen peroxide solution has a peroxide concentration of 1.1 percent by weight and a pH of 3.50 when used as a neutralizer for a waving/straightening solution with 4.3% by weight of available sulfur dioxide.

* * * * *